(12) United States Patent
Faehsing

(10) Patent No.: US 11,974,799 B2
(45) Date of Patent: May 7, 2024

(54) ELECTROSURGICAL SYSTEM WITH STORED PHASE CORRECTION VALUES

(71) Applicant: OLYMPUS WINTER & IBE GMBH, Hamburg (DE)

(72) Inventor: Thomas Faehsing, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 782 days.

(21) Appl. No.: 17/051,694

(22) PCT Filed: May 4, 2019

(86) PCT No.: PCT/EP2019/061469
§ 371 (c)(1),
(2) Date: Oct. 29, 2020

(87) PCT Pub. No.: WO2019/233683
PCT Pub. Date: Dec. 12, 2019

(65) Prior Publication Data
US 2021/0228259 A1 Jul. 29, 2021

(30) Foreign Application Priority Data
Jun. 4, 2018 (DE) ................. 10 2018 113 261.1

(51) Int. Cl.
*A61B 18/12* (2006.01)
*A61B 17/32* (2006.01)
(Continued)

(52) U.S. Cl.
CPC .. *A61B 18/1206* (2013.01); *A61B 17/320092* (2013.01); *A61B 18/1445* (2013.01);
(Continued)

(58) Field of Classification Search
CPC ............ A61B 18/1206; A61B 18/1445; A61B 17/320092; A61B 2017/0003;
(Continued)

(56) References Cited

U.S. PATENT DOCUMENTS

| 2002/0062132 A1 | 5/2002 | Kramer et al. |
| 2002/0165680 A1* | 11/2002 | Wiener .......... A61B 17/320068 |
| | | 702/75 |

(Continued)

FOREIGN PATENT DOCUMENTS

| EP | 1 199 044 A1 | 4/2002 |
| EP | 1 199 047 A2 | 4/2002 |

OTHER PUBLICATIONS

Kim et al., "Development of an Accurate Resonant Frequency Controlled Wire Ultrasonic Surgical Instrument", May 28, 2020, MDPI Sensors, pp. 1-19 (Year: 2020).*

(Continued)

*Primary Examiner* — Emily P Pham
(74) *Attorney, Agent, or Firm* — Oliff PLC

(57) ABSTRACT

An electrosurgical system having an ultrasound generator, configured to emit a high-frequency electrical signal, and an ultrasound instrument, including an ultrasound transducer configured to convert the signal into an ultrasound oscillation, wherein the generator is further configured to determine a resonance frequency of the transducer and adapt a frequency of the signal to the resonance frequency, and wherein the generator is further configured to detect a phase position between the current and the voltage of the signal and based on the detected phase position to determine whether the frequency of the signal corresponds to the resonance frequency. To enable the resonance frequency of the transducer to be determined correctly irrespective of component tolerances, the electrosurgical system is characterized in that the generator is configured to consider, during (Continued)

Figure 1:
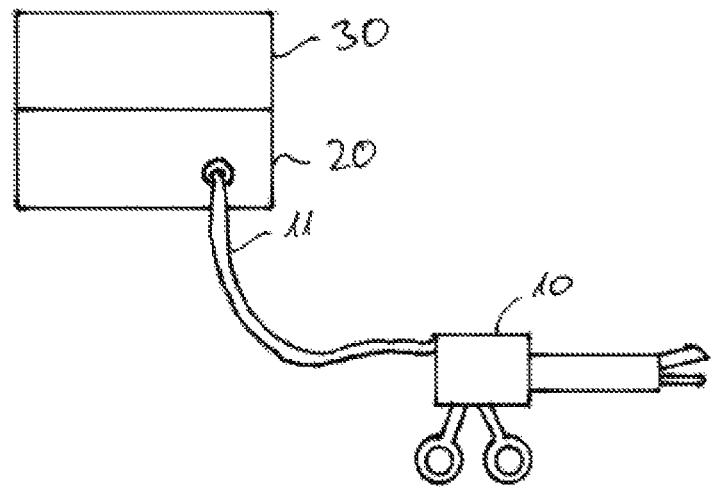

determination of the phase position, correction values, which are or can be stored in a memory of the generator and/or of the instrument.

8 Claims, 3 Drawing Sheets

(51) Int. Cl.
 *A61B 18/14* (2006.01)
 *A61B 17/00* (2006.01)
 *A61B 18/00* (2006.01)
(52) U.S. Cl.
 CPC ............... *A61B 2017/0003* (2013.01); *A61B 2017/00106* (2013.01); *A61B 2017/00181* (2013.01); *A61B 2018/00642* (2013.01); *A61B 2018/00684* (2013.01); *A61B 2018/00732* (2013.01); *A61B 2018/00827* (2013.01); *A61B 2018/00869* (2013.01); *A61B 2018/00892* (2013.01); *A61B 2018/00994* (2013.01)
(58) Field of Classification Search
 CPC ........... A61B 2017/00106; A61B 2017/00181; A61B 2017/00017; A61B 2018/00642; A61B 2018/00684; A61B 2018/00732; A61B 2018/00827; A61B 2018/00869; A61B 2018/00892; A61B 2018/00994
 See application file for complete search history.

(56) References Cited

U.S. PATENT DOCUMENTS

| | | |
|---|---|---|
| 2016/0324537 A1 | 11/2016 | Green et al. |
| 2017/0000516 A1 | 1/2017 | Stulen et al. |
| 2022/0039891 A1* | 2/2022 | Stulen .................... A61B 18/12 |

OTHER PUBLICATIONS

Feb. 19, 2019 Office Action issued in German Patent Application No. 10 2018 113 261.1.

Jul. 31, 2019 International Search Report issued in International Patent Application No. PCT/EP2019/061469.

Jul. 31, 2019 Written Opinion of the International Searching Authority issued in International Patent Application No. PCT/EP2019/061469.

* cited by examiner

ELECTROSURGICAL SYSTEM WITH STORED PHASE CORRECTION VALUES

The invention relates to an electrosurgical system having an ultrasound generator that is configured to output a high-frequency electrical signal, and an ultrasound instrument that includes an ultrasound transducer which is configured to convert the high-frequency electrical signal into an ultrasound oscillation, wherein the ultrasound generator is also configured to determine a resonance frequency of the ultrasound transducer and to adapt a frequency of the high-frequency electrical signal to this resonance frequency, and wherein the ultrasound generator is further configured to detect a phase position between the current and the voltage of the high-frequency electrical signal and to use the detected phase position to determine whether the frequency of the high-frequency electrical signal corresponds to the resonance frequency of the ultrasound transducer.

The invention also relates to an ultrasound generator and an ultrasound instrument.

In modern electrosurgery, in addition to pure electrosurgical procedures, in which a surgical effect is achieved exclusively through electrical currents, procedures and instruments are also used in which a high-frequency electrical signal is converted into an ultrasound vibration by means of an ultrasound transducer, which then causes a surgical effect. A surgical effect caused by the flow of current and a surgical effect caused by ultrasound can be combined.

Corresponding electrosurgical systems have an ultrasound generator for this purpose. This ultrasound generator generates a high-frequency electrical signal which is fed to an ultrasound instrument. The ultrasound instrument comprises an ultrasound transducer, which is usually a piezoelectrical element, which generates an ultrasound oscillation when the high-frequency electrical signal is applied. The ultrasound oscillation is transmitted to a working element in the ultrasound instrument, which has a surgical effect when it comes into contact with biological tissue. The working element is also referred to as a sonotrode.

In order to achieve an effective surgical effect, the ultrasound transducer is operated at its resonance frequency. This resonance frequency depends on the one hand on the type of ultrasound instrument, but on the other hand also on manufacturing tolerances of the components of the ultrasound instrument and on external factors such as the mechanical load during use of the ultrasound instrument. The resonance frequency is usually between 10 kHz and 100 kHz, for example 50 kHz.

In order to be able to energize the ultrasound transducer with its resonance frequency, the ultrasound generator is configured to determine this resonance frequency. For this purpose, the ultrasound generator performs a so-called scan process when the ultrasound instrument is not under load, in which the ultrasound transducer is energized with different frequencies. Since the strength of the mechanical ultrasound vibration cannot be measured directly, the ultrasound generator constantly measures the current and voltage of the high-frequency electrical signal and determines the phase position between the two variables. The phase position can be used to determine whether the frequency of the high-frequency electrical signal corresponds to the resonance frequency of the ultrasound transducer. At the resonance frequency, the current and voltage of the high-frequency signal are in phase.

During use, the resonance frequency changes due to changing mechanical loads on the ultrasound instrument. In order to track the frequency of the high-frequency electrical signal when the resonance frequency changes, the ultrasound generator continues to measure the phase position of the current and voltage and regulates the frequency so that the phase position determined in the scanning process is retained.

When measuring the phase position between current and voltage of the electrical signal, systematic measurement errors occur, which are caused by frequency responses and tolerances of the electronic components used. It can therefore happen that the ultrasound transducer is not operated precisely at its resonance frequency. This leads to a reduced effectiveness of the ultrasound instrument, wherein the ultrasound generator and the ultrasound instrument are stressed and possibly damaged by the power loss that occurs.

It is therefore the object of the invention to provide an electrosurgical system which is improved with regard to the problems described.

According to a first aspect of the invention, this object is achieved by an electrosurgical system with an ultrasound generator, which is configured to output a high-frequency electrical signal, and an ultrasound instrument, which comprises an ultrasound transducer, which is set up to convert the high-frequency electrical signal into an ultrasound oscillation, wherein the ultrasound generator is further configured to determine a resonance frequency of the ultrasound transducer and to adapt a frequency of the high-frequency electrical signal to this resonance frequency, and wherein the ultrasound generator is further configured to detect a phase position between the current and the voltage of the high-frequency electrical signal and use the determined phase position to determine whether the frequency of the high-frequency electrical signal corresponds to the resonance frequency of the ultrasound transducer, and which is further developed in that the ultrasound generator is configured, when determining the phase position, to consider correction values that are stored or can be stored in a memory of the ultrasound generator and/or the ultrasound instrument.

The correction values can be, for example, fixed amounts which are added to a phase position measured by the ultrasound generator in order to obtain a corrected phase position which is used for frequency regulation.

The correction values can also contain parameters of correction functions that map a phase correction as a function of various operating parameters of the ultrasound generator, for example as a function of the operating frequency or the output power of the ultrasound generator.

In one possible embodiment of the invention, the ultrasound generator can have sensors for measuring the current and/or the voltage of the high-frequency signal, wherein a frequency and/or phase response of the sensors influence the detection of the phase position between the current and the voltage of the high-frequency electrical signal, and wherein the correction values include first correction values which, when considered, fully or partially compensate for this influence.

The measuring circuits can include, for example, analog filters, analog-digital converters, and/or digital filters. A phase shift of the measured values caused by such elements can be determined theoretically very precisely or detected by measurement during the calibration of an ultrasound generator. The detected values can be stored as first correction values in a memory of the ultrasound generator and are thus available at any time to enable a corrected determination of the phase position between current and voltage of the high-frequency electrical signal.

According to a further advantageous embodiment of the invention, the ultrasound transducer represents a capacitive load, and the ultrasound generator includes an inductance in order to suppress reactive currents caused by the capacitive load, wherein a mismatch between the capacitive load and the inductance influences the determination of the phase position between the current and the voltage of the high-frequency electrical signal, and wherein the correction values include second correction values which, when considered, fully or partially compensate for this influence.

Ultrasound transducers generally have a capacitive behavior which is essentially characterized by a parallel capacitance that is independent of the mechanical behavior of the ultrasound transducer. To reduce the reactive currents caused by this capacitance, an inductance is connected in parallel to the ultrasound transducer at the output of many ultrasound generators. However, since the parallel capacitance of the ultrasound transducer is subject to manufacturing fluctuations, mismatches between the ultrasound transducer and the ultrasound generator can occur, which influence the phase position between the current and the voltage of the high-frequency electrical signal.

In order to compensate for this, the exact parallel capacitance of an ultrasound transducer can be determined after its manufacture and stored in the memory as a second correction value. This can then be considered by the ultrasound generator when determining the phase position.

In a preferred embodiment of the invention, the second correction values can be stored in the ultrasound instrument, and the ultrasound generator can be configured to read out the second correction values when the ultrasound instrument is connected to the ultrasound generator.

It is thereby possible to determine and store the second correction values without it being established with which ultrasound generator the respective ultrasound instrument is to be used. This makes the electrosurgical system very flexible.

It is also conceivable, when an ultrasound instrument is first connected to an ultrasound generator, to measure the resulting phase influence and to store it as a second correction value in a memory element of the ultrasound generator or of the ultrasound instrument. The ultrasound generator can then read this phase influence from the memory when the same ultrasound instrument is used later and consider it accordingly.

In an advantageous embodiment of the invention, an ultrasound generator can comprise several inductances, which can be optionally switched on or off depending on a type of an attached ultrasound instrument. In this way, an ultrasound generator can be operated in an optimally adapted manner with different types of ultrasound instruments.

The connection or disconnection of inductances can preferably take place on the basis of an automatic instrument detection. For this purpose, for example, identification data can be stored in a memory element of the ultrasound instrument, on the basis of which the ultrasound generator detects the type of instrument.

The first and/or second correction values are preferably determined, or can be determined, by way of a calibration measurement.

According to a particular embodiment of the invention, the ultrasound generator is configured to sample the current and voltage of the high-frequency electrical signal in a time-discrete manner and to determine the phase position from the curve of the sample values, wherein for the consideration of the correction values, the sample values of the current are delayed with respect to the sample values of the voltage by a time difference derived from the correction values, or the sample values of the voltage are delayed with respect to the sample values of the current by a time difference derived from the correction values.

With a corresponding time-discrete processing of the sampled values of current and voltage, the correction values can be taken into account particularly easily. The processing of the sampled values takes place preferably within the framework of a program executed in a processor that is part of the ultrasound generator. The sampled values to be delayed can be routed through a first-in-first-out (FIFO) data structure, wherein the time difference results from the product of the number of memory locations in the FIFO data structure and the clock rate of the program execution. A shift register can be used as the FIFO data structure, for example.

According to further aspects of the invention, the object is achieved by an ultrasound generator and/or an ultrasound instrument of an electrosurgical system according to the above explanations. With regard to the effects and advantages achieved in this way, express reference is made to what has been said above.

In the following, the invention shall be explained in more detail using some exemplary representations. The illustrated exemplary embodiments serve only to provide a better understanding of the invention without restricting it.

Figure 2:
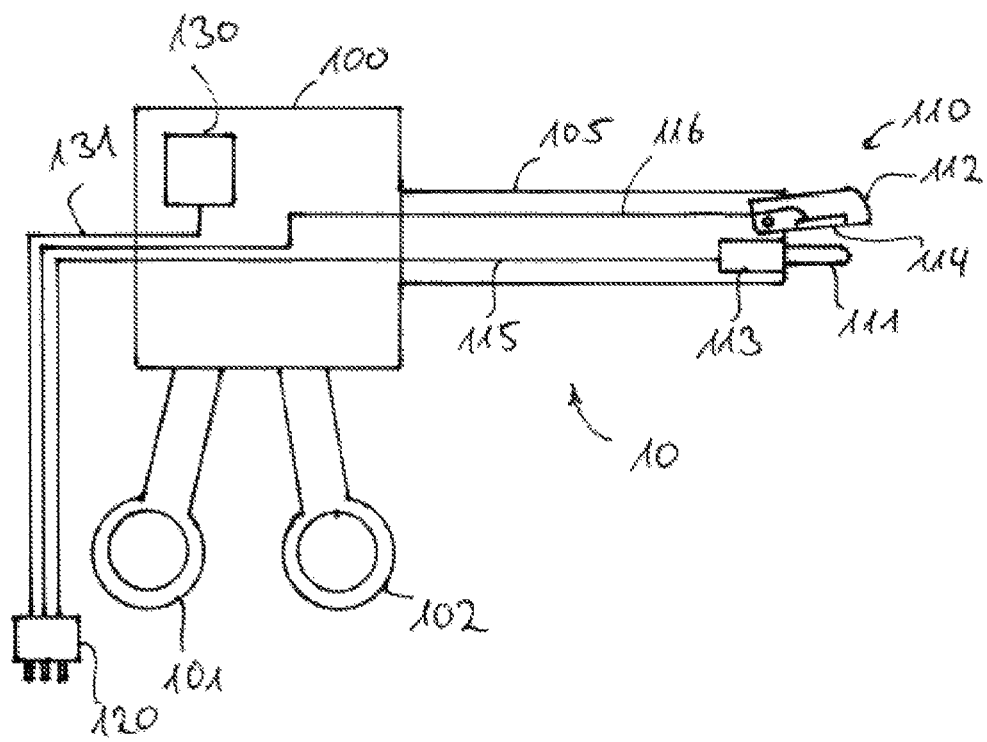
Figure 3:
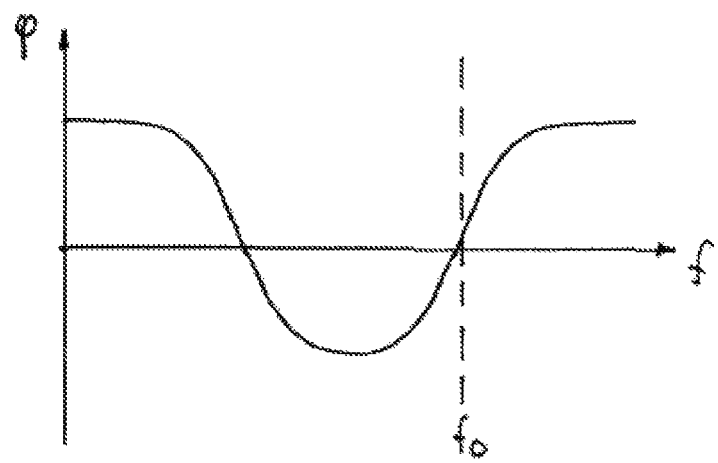
Figure 4:
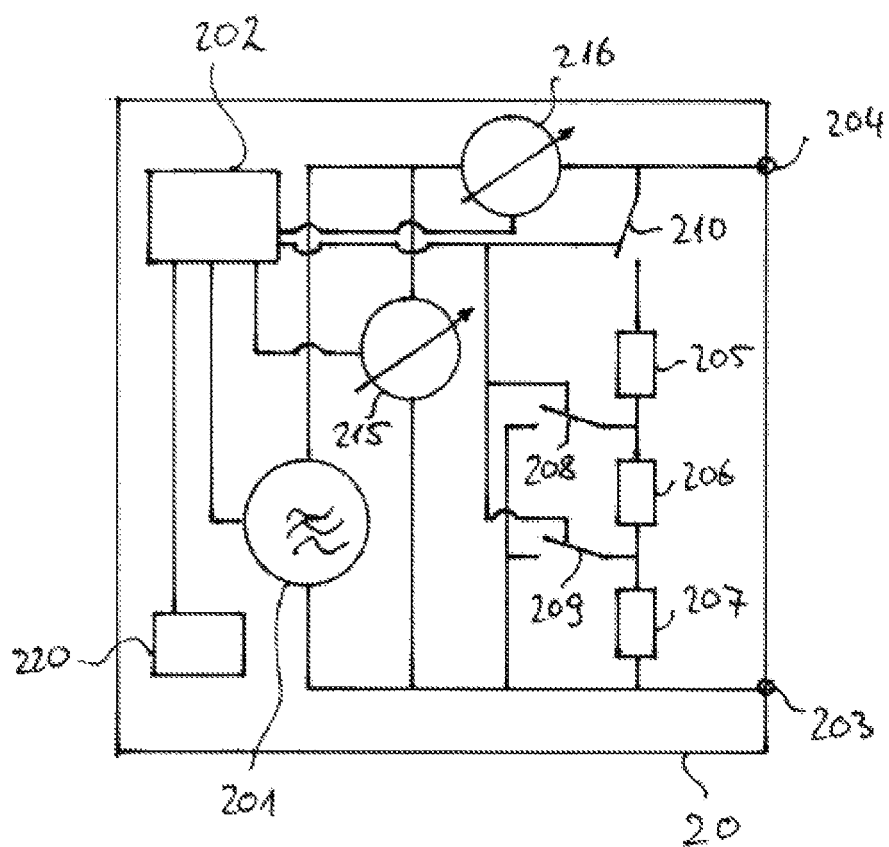
Figure 5:
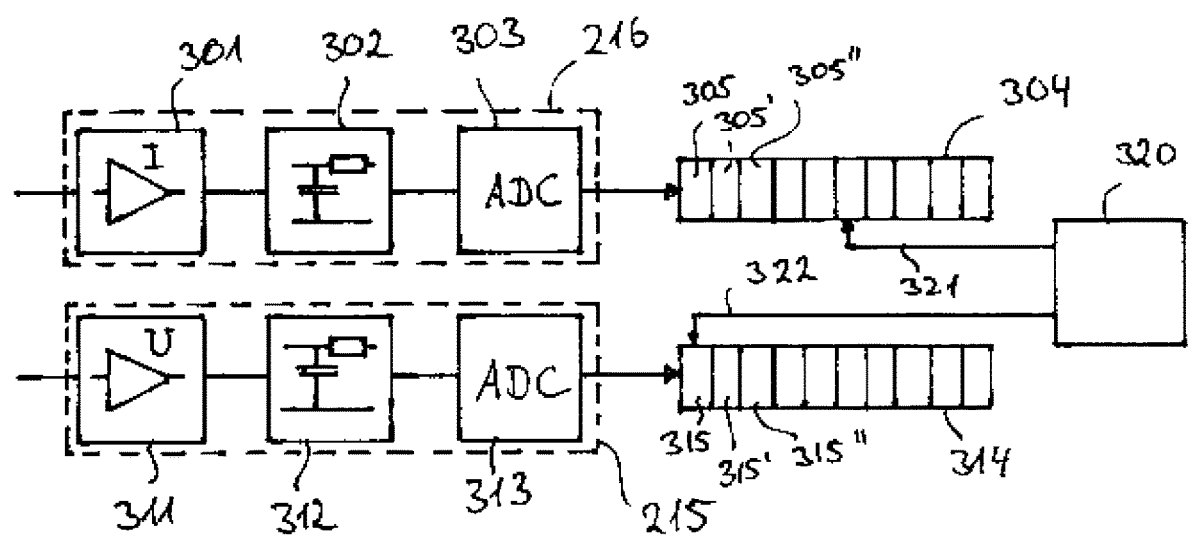

Shown in the drawings are:

FIG. 1: an electrosurgical system,
FIG. 2: the structure of an ultrasound instrument,
FIG. 3: phase response of an ultrasound transducer,
FIG. 4: schematic structure of an ultrasound generator,
FIG. 5: a possible sequence of phase correction.

FIG. 1 shows an electrosurgical system having an ultrasound instrument 10, an ultrasound generator 20, and a high-frequency generator 30. The ultrasound instrument 10 is connected to the ultrasound generator 20 via a cable 11.

The ultrasound instrument 10 can, for example, be a combined high-frequency and ultrasound forceps, such as those sold by Olympus Corporation under the name THUNDERBEAT.

During operation, the ultrasound generator 20 generates a first high-frequency electrical signal which is transmitted via the cable 11 to the ultrasound instrument 10, and there is converted into an ultrasound oscillation by an ultrasound transducer (not shown). The ultrasound oscillation is coupled into a sonotrode, not shown, which can be brought into direct or indirect contact with tissue to be treated.

The high-frequency generator 30 generates a second high-frequency electrical signal during operation, which is transmitted via an internal connection to the ultrasound generator 20 and from there, also via the cable 11, to the ultrasound instrument 10. In the ultrasound instrument 10, the second high-frequency electrical signal is fed to one or more electrodes, which can be brought into direct or indirect contact with the tissue to be treated.

In FIG. 2, the structure of the ultrasound instrument 10 is shown in more detail, wherein the illustration is not true to scale and is greatly simplified.

The ultrasound instrument 10 consists of a main body 100 with handle levers 101, 102. A shaft 105 adjoins the main body 100, at the distal end of which a forceps 110 is arranged.

The forceps 110 here comprises a fixed branch, which is formed by a sonotrode 111, and a movable branch 112. The sonotrode 111 is coupled to an ultrasound transducer 113. An electrode 114 is arranged on the movable branch 112.

The movable branch 112 can be moved in the direction of the sonotrode 111 by actuating one of the handle levers 101, 102, so that the forceps 110 closes. A section of human or animal tissue, not shown, which is clamped in the closed forceps 110, can then be treated by activating the sonotrode 111 and/or the electrode 114.

To activate the sonotrode 111, a first high-frequency electrical signal is fed from the ultrasound generator 20 to the ultrasound transducer 113. This converts the signal into an ultrasound oscillation and transmits this to the sonotrode 111. The mechanical movement of the sonotrode 111, which is in close contact with the tissue to be treated, then causes a surgical effect in the tissue, which can vary depending on the design of the sonotrode and the desired result.

To activate the electrode 114, a second high-frequency electrical signal is fed to it from the electrosurgical generator 30.

The electrical signals are supplied via lines 115, 116. The lines 115, 116 end in a plug 120 which can be connected to the ultrasound generator 20.

The ultrasound instrument 10 further comprises a memory element 130, the function of which will be explained later. The memory element 130 is also connected to the plug 120 via a line 131.

In order to achieve an optimal surgical effect, it is desirable that the ultrasound generator 20 energizes the ultrasound transducer 113 with its mechanical resonance frequency. This mechanical resonance frequency, however, depends on various parameters, for example manufacturing tolerances of the ultrasound transducer 113, but also on the type and quantity of the tissue gripped in the forceps 110 and the contact pressure of the movable branch 112.

In order to determine the current resonance frequency of the ultrasound transducer 113 at the beginning of an activation phase, the ultrasound generator 20 performs a so-called scan, wherein the ultrasound transducer is energized successively with several frequencies and the curve of the phase position of the current and voltage of the first high-frequency electrical signal is measured.

The course of the phase position p of current and voltage as a function of the frequency f is shown in FIG. 3. It can be seen that at a low frequency there is initially a positive phase position, that is, the current leads the voltage. As the frequency rises, the phase decreases, passes through the zero point, and becomes negative. In this frequency range, the voltage leads the current. When approaching the resonance frequency $f_0$, the phase p rises again and passes through the zero point again when the resonance frequency $f_0$ is reached, to become positive as the frequencies continue to rise. Here again the current leads the voltage.

The change of phase position at low frequencies is determined by a structure-related parallel capacitance. This is mainly caused by the capacitive effect of contacting surfaces that are vapor-deposited on the piezo crystals of the ultrasound transducer.

In FIG. 4, the structure of the ultrasound generator 20 is shown schematically insofar as it is relevant for understanding the invention.

An oscillator 201 generates a high-frequency electrical signal with a controllable frequency. The frequency of the oscillator 201 is controlled by a controller 202. The high-frequency electrical signal is provided at output terminals 203, 204, which can be connected to contacts of the plug 120 of the ultrasound instrument 10.

Inductances 205, 206, 207 are arranged between the output terminals 203, 204, which inductances can be switched on or off by switches 208, 209, 210. The inductances 205, 206, 207 serve to compensate for the phase shift between the current and voltage of the high-frequency electrical signal, which is caused by the parallel capacitance of the ultrasound transducer 113. The switches 208, 209, 210 are controlled by the controller 202.

Depending on the design of a connected ultrasound instrument, all or some of the inductances 205, 206, 207 are activated by the control. A connected ultrasound instrument is detected using known methods for instrument recognition, which do not need to be explained in more detail here. For example, information stored in the memory 130 of the ultrasound instrument 10 can be evaluated.

The current and the voltage of the high-frequency electrical signal are scanned at short intervals via sensors 215, 216. From the sampled values, the controller 202 determines the phase position between current and voltage and regulates the frequency of the oscillator 201 so that the current and voltage are in phase in order to energize the ultrasound transducer 113 with its resonance frequency.

As was explained at the beginning, both the measurement of the phase position and the compensation of the parallel capacitance are subject to inaccuracies. The sensors 215, 216 comprise electronic sensors with integrated filters, which themselves can lead to certain phase shifts in the measurement results. In addition, the parallel capacitances of connected ultrasound transducers 113 fluctuate due to manufacturing tolerances. This results in mismatches, which in turn distort the phase position between current and voltage of the high-frequency electrical signal.

In order to precisely determine the resonance frequency of the ultrasound transducer 113 during the scanning process despite the described inaccuracies in the phase measurement, and to be able to track the operating frequency of the oscillator 201 accordingly, the controller 202 can, when determining the phase position between current and voltage of the high-frequency electrical signal, consider correction values. For this purpose, a memory element 220 is provided in the ultrasound generator 20, in which corresponding correction values can be stored.

One possibility for considering the correction values is shown schematically in FIG. 5. The sensor 216 for the current comprises a measuring amplifier 301, a low-pass filter 302, and an analog-digital converter 303. The analog-digital converter 303 converts the output voltage of the low-pass filter 302 at a fixed sampling rate into digital sampling values, wherein the cutoff frequency of the low-pass filter 302 is adapted to the sampling rate.

The sampled values from the analog-digital converter 303 are stored in a shift register 304. The shift register 304 comprises a plurality of register cells 305, 305', 305", etc., which can each receive one sample value.

Each time a new sample is stored in shift register 304, samples already stored there are shifted one register cell further to the right.

In a corresponding manner, the sensor 215 for the voltage comprises a measuring amplifier 311, a low-pass filter 312, and an analog-digital converter 313. Samples from the analog-digital converter 313 are stored in a shift register 314 with register cells 315, 315', 315", etc. The mode of operation corresponds to the mode of operation of the shift register 304 described above.

A unit 320 for determining the phase position between current and voltage now accesses the contents of the shift registers 304, 314 and reads out successive sample values for the current and the voltage. With the aid of the correction values stored in the memory 220, it is determined at which point of the shift register 304, 314 corresponding sampled values are read out.

If, for example, a positive phase shift, that is, an advance of the current caused by the effects described above, has to be corrected, the sampled values of the current are read out from a register cell of the shift register 304 located further to the right than the sampled values of the voltage from the shift register 314. This is indicated by the differently positioned read pointers 321, 322.

In the example shown, the sample value of the current is read out from the sixth register cell of the shift register 304, whereas the sample value of the voltage is read out from the first register cell of the shift register 314. As a result, the current signal is delayed by five times the sampling rate of the analog-digital converter 303, 313 before the phase position is detected.

If, however, an advance of the voltage is to be corrected, the sample value of the current is read out from the first register cell of the shift register 314, and the sample value of the voltage is read out from a register cell of the shift register 304 located further to the right.

The actual determination of the phase position of the current and voltage by the unit 320 can take place in various known ways and include methods such as autocorrelation, fast Fourier transformation or the like.

The shift registers 304, 314 can be provided as discrete components, and the unit 320 can be implemented as a digital signal processor. Alternatively, the shift registers 304, 314 and the unit 320 can be implemented by software, which is executed in the controller 202 of the ultrasound generator 20. Other hardware-based implementations are also conceivable, for example using field-programmable gate arrays (FPGA)

In order to determine the correction values required for the phase compensation, the phase responses of the low-pass filters 302, 312 can be measured during commissioning of the ultrasound generator 20. For this purpose, for example, the ultrasound generator can be operated on a purely ohmic load. The required correction values can then be determined from the phase responses, for example in the form of a lookup table in which corresponding delay times are stored for various working frequencies and are stored in the memory 220.

In order to compensate for a phase influence due to mismatches between the inductances 205, 206, 207 and the parallel capacitance of an ultrasound transducer 113, the size of the mismatch must be known. For this purpose, when an ultrasound instrument 10 is connected to an ultrasound generator 20 for the first time, the mismatch can be measured, from which the correction values can then be determined.

Alternatively, during the manufacture of the ultrasound instrument 10, the parallel capacitance of the ultrasound transducer 113 can be precisely measured and stored in the memory 130 of the ultrasound instrument. Likewise, during the manufacture of the ultrasound generator 20, the inductances 205, 206, 207 can be precisely measured and stored in the memory 220 of the ultrasound generator 20.

When the ultrasound instrument 10 is connected to the ultrasound generator 20, the controller 202 of the ultrasound generator reads the value of the parallel capacitance from the memory 130 and the values of the inductances 205, 206, 207 from the memory 220, and calculates the mismatch resulting from these values and the corresponding correction values. These correction values can then be used for phase correction in the manner described above.

The invention claimed is:

1. An electrosurgical system comprising:
    an ultrasound generator which is configured to emit a high-frequency electrical signal, and
    an ultrasound instrument which comprises an ultrasound transducer which is configured to convert the high-frequency electrical signal into an ultrasound oscillation, wherein the ultrasound generator is further configured to determine a resonance frequency of the ultrasound transducer and to adapt a frequency of the high-frequency electrical signal to this resonance frequency, and wherein the ultrasound generator is further configured to determine a phase position between the current and the voltage of the high-frequency electrical signal and to use the determined phase position to determine whether the frequency of the high-frequency electrical signal corresponds to the resonance frequency of the ultrasound transducer,
    wherein the ultrasound generator is configured to determine the phase position based on correction values, which are stored in a memory of the ultrasound generator and/or the ultrasound instrument.

2. The electrosurgical system according to claim 1, wherein the ultrasound generator comprises sensors for measuring the current and/or the voltage of the high-frequency signal, wherein a frequency and/or phase response of the sensors influences the determination of the phase position between the current and the voltage of the high-frequency electrical signal, and wherein the correction values include first correction values, which, when taken into account, fully or partially compensate for this influence.

3. The electrosurgical system according to claim 1, wherein the ultrasound transducer represents a capacitive load, and that the ultrasound generator comprises an inductance, in order to suppress reactive currents caused by the capacitive load, wherein a mismatch between the capacitive load and the inductance influences the determination of the phase position between the current and the voltage of the high-frequency electrical signal, and wherein the correction values include second correction values, which, when taken into account, fully or partially compensate for this influence.

4. The electrosurgical system according to claim 3, wherein the second correction values are stored in the ultrasound instrument, and that the ultrasound generator is configured to read out the second correction values when the ultrasound instrument is connected to the ultrasound generator.

5. The electrosurgical system according to claim 3, wherein the ultrasound generator comprises several inductors which can be optionally switched on or off depending on a type of an attached ultrasound instrument.

6. The electrosurgical system according to claim 5, wherein the inductances are switched on and/or off on the basis of automatic instrument detection.

7. The electrosurgical system according to claim 1, wherein the first and/or the second correction values are determined or can be determined by a calibration measurement.

8. The electrosurgical system according to claim 1, wherein the ultrasound generator is configured to sample the current and voltage of the high-frequency electrical signal in a time-discrete manner and to determine the phase position from the curve of the sample values, wherein for consideration of the correction values,
    the sampled values of the current are delayed with respect to the sampled values of the voltage by a time difference derived from the correction values, or
    the sampled values of the voltage are delayed with respect to the sampled values of the current by a time difference derived from the correction values.

* * * * *